(12) United States Patent
Schnall

(10) Patent No.: US 9,474,453 B2
(45) Date of Patent: Oct. 25, 2016

(54) MEASURING BLOOD FLOW AND VENOUS CAPACITANCE

(75) Inventor: Robert P. Schnall, Kiryat-Bialik (IL)

(73) Assignee: Itamar Medical Ltd., Caesarea (IL)

( * ) Notice: Subject to any disclaimer, the term of this patent is extended or adjusted under 35 U.S.C. 154(b) by 1713 days.

(21) Appl. No.: 11/662,610

(22) PCT Filed: Sep. 15, 2005

(86) PCT No.: PCT/IL2005/000993
§ 371 (c)(1),
(2), (4) Date: Mar. 13, 2007

(87) PCT Pub. No.: WO2006/030441
PCT Pub. Date: Mar. 23, 2006

(65) Prior Publication Data
US 2008/0077024 A1   Mar. 27, 2008

Related U.S. Application Data

(60) Provisional application No. 60/609,813, filed on Sep. 15, 2004.

(51) Int. Cl.
*A61B 5/02* (2006.01)
*A61B 5/029* (2006.01)
(Continued)

(52) U.S. Cl.
CPC ........... *A61B 5/02241* (2013.01); *A61B 5/029* (2013.01); *A61B 5/6826* (2013.01); *A61B 5/6838* (2013.01); *A61B 5/7285* (2013.01); *A61B 2560/0261* (2013.01)

(58) Field of Classification Search
USPC ................ 600/481–485, 488, 490, 492–496, 600/499–500
See application file for complete search history.

(56) References Cited

U.S. PATENT DOCUMENTS 4,134,396 A * 1/1979 Doll .............................. 600/504
4,548,211 A   10/1985 Marks
(Continued)

FOREIGN PATENT DOCUMENTS

JP       05-056902      3/1993
WO    WO 02/24053 A3 *   3/2002   ............... A61B 5/00
(Continued)

OTHER PUBLICATIONS

Brown et al. Filling and emptying of the low-pressure blood vessels of the human forearm. Jounal of Applied Physiology. Mar. 1966. 21(2): 573-82.*

(Continued)

*Primary Examiner* — Navin Natnithithadha
*Assistant Examiner* — Eric Messersmith

(57) ABSTRACT

Non-invasively measuring a physiological parameter by applying to a subject's body part a venous occlusion plethysmographic device including a first section having a first fluid chamber and at least a second region having a second fluid chamber to engage a first region of the body part and a second region of the body part, proximal of the first region; pressurizing the first chamber to a pressure sufficient to compensate for hydrostatic pressure added to the inherent venous pressure at the maximal vertical lowering level of the body part relative to the subject's heart level; intermittently raising and lowering the pressure in the second fluid chamber to a pressure above or equal to the pressure in the first chamber, but below the arterial blood pressure; measuring changes in volume of the first region of the body part; and utilizing the measured volume changes to provide a measure of the physiological parameter.

31 Claims, 6 Drawing Sheets

(51) Int. Cl.
*A61B 5/022* (2006.01)
*A61B 5/00* (2006.01)

(56) References Cited

U.S. PATENT DOCUMENTS

| | | | |
|---|---|---|---|
| 6,319,205 B1 * | 11/2001 | Goor et al. | 600/485 |
| 7,374,540 B2 | 5/2008 | Schnall | |
| 7,819,811 B2 | 10/2010 | Schnall | |
| 2003/0109772 A1 | 6/2003 | Mills | |
| 2004/0044290 A1 | 3/2004 | Ward et al. | |
| 2010/0004546 A1 | 1/2010 | Tanaka et al. | |
| 2014/0336517 A1 | 11/2014 | Schnall et al. | |

FOREIGN PATENT DOCUMENTS

| WO | WO 02/080752 A2 * | 10/2002 |
|---|---|---|
| WO | WO 2004/086963 | 10/2004 |
| WO | WO 2013/076722 | 5/2013 |

OTHER PUBLICATIONS

Joyner et al. From Belfast to Mayo and beyond: the use and future of plethysmography to study blood flow in human limbs. Journal of Applied Physiology. 2001. 91: 2431-2441.*

Wallace, William F. M., "Does the Hydrostatic Pressure of the Water in a Venous Occlusion Plethysmograph Affect the Apparent Rate of Blood Flow to the Forearm?", 1958, J. Physiol. 143, 380-385.*

Response Dated Oct. 7, 2010 to Communication Pursuant to Article 94(3) EPC of Jul. 7, 2010 From the European Patent Office Re. Application No. 05779418.2.

Communication Pursuant to Article 94(3) EPC Dated Jul. 7, 2010 From the European Patent Office Re. Application No. 05779418.2.

International Preliminary Report on Patentability Dated Mar. 29, 2007 From the International Bureau of WIPO Re.: Application No. PCT/IL2005/000993.

Res to WO of Sep. 18, 2006.

Supplementary Search Report of Jan. 16, 2008.

Communication Pursuant to Article 94(3) EPC Dated Jan. 29, 2014 From the European Patent Office Re. Application No. 05779418.2.

International Preliminary Report on Patentability Dated Jun. 5, 2014 From the International Bureau of WIPO Re. Application No. PCT/IL2012/050466.

International Search Report and the Written Opinion Dated Mar. 19, 2013 From the International Searching Authority Re. Application No. PCT/IL2012/050466.

Requisition by the Examiner Dated May 10, 2012 From the Canadian Intellectual Property Office Re. Application No. 2,505,136.

Requisition by the Examiner Dated May 25, 2012 From the Canadian Intellectual Property Office Re. Application No. 2,580,399.

Requisition by the Examiner Dated Jan. 31, 2014 From the Canadian Intellectual Property Office Re. Application No. 2,580,399.

Translation of Notice of Reason for Rejection Dated Sep. 14, 2012 From the Japanese Patent Office Re. Application No. 2001-563003.

Axtell et al. "Assessing Endothelial Vasodilator Function With the Endo-PAT 2000", Journal of Visualized Experiments, 44: e2167-1-e2167-5, Oct. 2010.

* cited by examiner

LOW PROBE PRESSURE
NO VENOUS OCCLUSION

POSITIVE PROBE PRESSURE
NO VENOUS OCCLUSION

LOW PROBE PRESSURE
WITH VENOUS OCCLUSION

POSITIVE PROBE PRESSURE
WITH VENOUS OCCLUSION

MEASURING BLOOD FLOW AND VENOUS CAPACITANCE

RELATED APPLICATIONS

This Application is a National Phase of PCT Patent Application No. PCT/IL2005/000993 having International Filing Date of Sep. 15, 2005, which claims the benefit of U.S. Provisional Patent Application No. 60/609,813 filed on Sep. 15, 2004. The contents of the above Applications are all incorporated herein by reference.

FIELD AND BACKGROUND OF THE PRESENT INVENTION

The present invention relates to a method and apparatus for non-invasively measuring certain physiological parameters of a subject. The invention is particularly useful in venous occlusion plethysmography (VOP) for measuring volumetric blood flow, or other physiological parameters derived from volumetric blood flow, as well as providing certain-quantitative indices of venous compliance, and is therefore described below with respect to such applications.

Venous occlusion plethysmography is a known method for non-invasively measuring a physiological parameter of a subject, particularly volumetric blood flow. It is based on the accumulation of blood in the veins of a body region that is distal or upstream from a venous occlusion device. In the venous occlusion plethysmography method, a pressure greater than the venous pressure, but less than the arterial pressure, is applied around a body region in order to cause venous blood to be accumulated in another body region located distally (or further away from the heart) to the one acted upon by the venous occlusion device. Changes in volume with respect to time of the distal region are measured and utilized to provide a measure of the blood flow, or other physiological parameters derived therefrom such as the relative volume accumulated at a given occlusion pressure level.

VOP is based on the following physiological properties of a subject's circulatory system:

1. the veins possess very high levels of compliance and are able to accommodate large amounts of blood at relatively low pressure;
2. there is a large pressure difference between systemic arterial and systemic venous blood pressure; and
3. blood flow in the systemic arteries propagates from the heart toward the periphery of the body, whereas it propagates in the opposite direction in the system veins, (i.e. from the periphery towards the heart).

At the present time, VOP measurements are generally made by inflating a segmental cuff, placed over the perimeter of a body region, to apply pressure over the entire circumference of the particular body region, to a pressure between venous and arterial pressure, and then measuring the volume of blood which accumulates distal to the cuff. As described more particularly below, when the venous occlusion pressure is intermittently raised in the cuff, the cumulative volume begins to increase with each pulse wave, until such time as the veins are unable to accommodate more volume.

As mentioned, the veins are characterized as having a very high degree of compliance compared to arterial blood vessels; that is, they are capable of undergoing a larger volume change for a given increase in pressure compared to equivalent sized arterial vessels. Compliance of the veins is especially high after they have initially been emptied. However as the veins become increasingly filled, and the venous wall begins to be stretched, the ability of the veins to expand without increasing the pressure of the contained blood tends to be reduced, upon pressure increases, thereby resulting in a non-linear pressure versus volume relationship. Nevertheless, a substantial portion of the volume of blood which the veins are able to accommodate from their fully emptied state, occurs without the venous wall being stretched, and this occurs at a very low level of pressure. The rate of change of the accumulated blood volume is the volumetric blood flow (BF). When the blood in the region distal to the occlusion cuff reaches the cuff pressure, further accumulation of blood ceases, and a steady state level of blood volume prevails. The volume of accumulated blood distal to the occlusion cuff at that point thus reaches a plateau which represents the venous capacitance (VC).

It is to be particularly noted that as the volume and pressure of the blood distal to the venous occlusion cuff increases, the compliance of the veins tends to decrease.

A major limitation of VOP, as it is currently practiced, is that it is restricted to measurements in body parts which are maintained above heart level, for the following reason: The combination of extremely high venous compliance described above, and the generation of hydrostatic gradients in the vascular system due to vertical displacement relative to heart level, means that the veins in body parts which are below heart level easily become filled with blood and therefore lose the capacity to freely accommodate additional volumes of blood. When venous blood vessels become filled due to hydrostatic pressure gradients, the partially filled veins cannot be accurately used for VOP measurements due to the relative reduction in the ability to further expand and the lack of linearity of the pressure volume relationship because of vessel wall stretching. For these reasons, VOP measurements have until now been strictly limited to the above heart position of the measured region.

While the filling of the veins due to such hydrostatic pressures can be prevented by the application of a sufficient level of external counter pressure to the measurement site (so as to counterbalance the intra-venous pressure), traditional VOP volumetric collecting cups are mechanically incapable of being pressurized to any appreciable degree without being forced off the measurement site. They are therefore unable to provide the necessary degree of pressure to counterbalance the intra-venous pressure, and thus cannot be used to reliably measure BF below heart level. Substitute collecting devices, such as mercury in silastic rings or circumferential strain gauges, provide no actual pressure field to the bulk of the tissues distal to the venous occlusion cuff, so that resting venous distention cannot be counterbalanced by any of these methods. Furthermore, since they do not actually measure volume but rather an index of circumference, they are not capable of being accurately calibrated to provide an index of volume.

Because of these limitations, traditional VOP devices are not able to modify the local venous transmural blood pressure so as to allow BF measurements or venous capacitance at specific pressure levels to be made when the measured body part is below heart level, and therefore, as noted above, VOP measurements have generally been limited to body regions which are located above the subject's heart or are deliberately elevated above heart level.

Further information regarding VOP measurements is available from the patent literature, e.g. U.S. Pat. Nos. 5,447,161 and 6,749,567, the contents of which are incorporated herein by reference. These patents also describe other physiological parameters derived from volumetric blood flow which may also be measured by the VOP method.

OBJECTS AND BRIEF SUMMARY OF THE PRESENT INVENTION

An object of the present invention is to provide a method having advantages in the above respects for non-invasively measuring physiological parameters, particularly volumetric blood flow and venous capacitance. A more particular object of the present invention is to provide a VOP measurement process which is not limited to body parts above the heart level of the subject, or those elevated to be above heart level. Another object of the present invention is to provide apparatus for making such non-invasive measurements in accordance with the novel method. Yet another object of the present invention is to provide apparatus for making such non-invasive measurements in a quantitative manner to provide data in standard physical units.

According to one aspect of the present invention, there is provided a method for non-invasively measuring a physiological parameter of a subject, comprising: applying to a body part of the subject a venous occlusion plethysmographic device including a first section to engage a distal region of the body part including its distal tip, and a second section to engage a proximal region of the body part, contiguous to said distal region at the side thereof facing the heart of the subject; pressurizing said first section to produce a static pressure field therein in which the pressure applied to at least a part of said first section exceeds the sum of the inherent venous pressure and the hydrostatic pressure prevailing within said body part; intermittently raising and lowering the pressure in said second section to a pressure above or equal to the pressure in said first section but below the arterial blood pressure; measuring changes in volume in said distal region of the body part; and utilizing the measured changes in volume to provide a measure of the physiological parameter.

Preferably, the venous occlusion device used in the above method is a peripheral arterial tonometry (PAT) probe, such as described in previously issued U.S. Pat. Nos. 6,319,205; 6,322,515; 6,461,305 and 6,488,633, the contents of which are incorporated herein by reference, and several currently pending patent applications, all assigned to the same assignee as the present application. The preferred embodiments of the invention described below thus illustrate the utilization of such PAT probes.

According to further features in the described preferred embodiments, the volume changes are accumulated over a measured time period, and the rate of change is determined to thereby provide a measurement of volumetric blood flow. As indicated above, however, the method could also be used for measuring other physiological parameters derived from volumetric blood flow, e.g. the level of venous capacitance at specific venous pressure levels, venous pressure, arterial pressure, etc., as described for example in the above-cited U.S. Pat. No. 5,447,161.

According to further features in the described preferred embodiments, said first section includes a first chamber for applying said static pressure to said distal region including its distal tip, and said second section includes a second chamber for applying said intermittently raised and lowered pressure to said proximal region.

According to one described preferred embodiment, said first chamber is configured to engage said distal region including its distal tip of the body part.

Other embodiments are described wherein said first section further includes a third chamber on the proximal side of said first chamber such that said first chamber pressurizes said distal region including its distal tip of the body part, and said third chamber pressurizes said distal region of the body part between said distal region including its distal tip and said proximal region. In one such described embodiment the pressures in said first and third chambers are the same and each exceeds the sum of the inherent venous pressure and the hydrostatic pressure prevailing within said body part. In a second described embodiment, the pressure in said first chamber is sufficient to arrest the circulation in said distal region including its distal tip, and the pressure in said third chamber exceeds the sum of the inherent venous pressure and the hydrostatic pressure prevailing within said body part.

According to yet another aspect of the present invention there is provided apparatus for non-invasively measuring a physiological parameter of a subject, comprising: a venous occlusion plethysmographic device including a first section to engage a distal region of the body part including the distal tip, and a second section to engage a proximal region of the body part, contiguous to said distal region including its distal tip at the side thereof facing the heart of the subject; a pressurizing system for pressurizing; said first section to produce a pressure field therein in which the pressure applied to at least a part of said section exceeds the sum of the inherent venous pressure and the hydrostatic pressure prevailing within said body part; and a control system for intermittently raising and lowering the pressure in the second section to a pressure above or equal to the pressure with said first section but below the arterial blood pressure, for measuring changes in volume of said first region of the body part, and for utilizing said measured volume changes to provide a measure of the physiological parameter.

Further features and advantages of the invention will be apparent from the description below.

BRIEF DESCRIPTION OF THE DRAWINGS

The invention is herein described, by way of example only, with reference to the accompanying drawings, wherein:

FIGS. 1a-1c include waveforms illustrating the basic venous occlusion plethysmography (VOP) process for measuring volumetric blood flow (BF) and venous capacitance or compliance; whereas

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

THE BASIC VENOUS OCCLUSION PLETHYSMOGRAPHY (VOP) PROCESS

As briefly described above, the VOP method for measuring a physiological parameter of a subject is based on applying to the circumference of a body region of the subject a venous occlusion device; intermittently raising and lowering the pressure to cause intermittent venous occlusion, the magnitude of the venous occlusion pressure being below the arterial pressure; and measuring changes in volume of the body region distal or upstream (away from the heart) of the body region whose veins are occluded by the occlusion device to provide a measure of the physiological parameter. This process is illustrated in FIGS. 1a-1d.

Figure 1A:
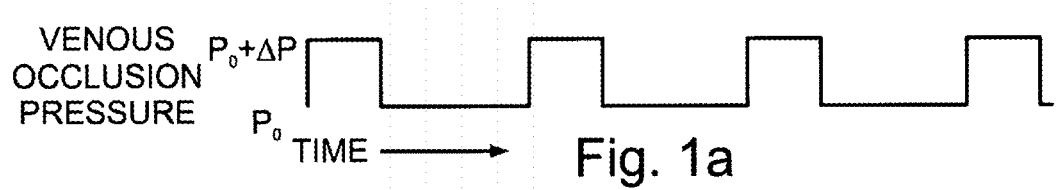
Figure 1B:
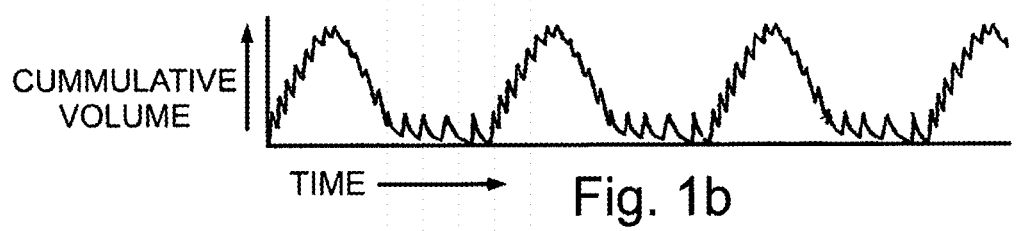
Figure 1C:
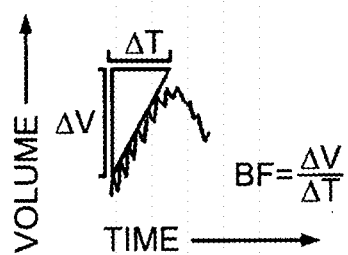

Thus, when the venous occlusion pressure is intermittently raised by the occlusion device (FIG. 1a), the cumulative volume begins to increase with each pulse wave (FIG. 1b). As shown in FIG. 1c, the rate of change of the accumulated blood volume is the volumetric blood flow (BF).

Generally speaking, the measured changes in volume are determined by measuring the volume change at some given pulsewave landmark over at least a single pulse cycle.

In practice, rate of change of the accumulated blood volume is determined by measuring the volume change at some given pulsewave landmark over a number of pulse cycles. Examples of appropriate pulse wave landmarks include the systolic peak, the foot of the pulse upstroke, the incisuria or dichrotic notch, and others. To allow for pulse to pulse volume change variability, it is common practice to determine a linear regression model line of best fit to optimally determine the volume changes for a multiplicity of pulse signals. The change of volume over time described by such a line of best fit represents the blood flow rate.

Figure 1D:
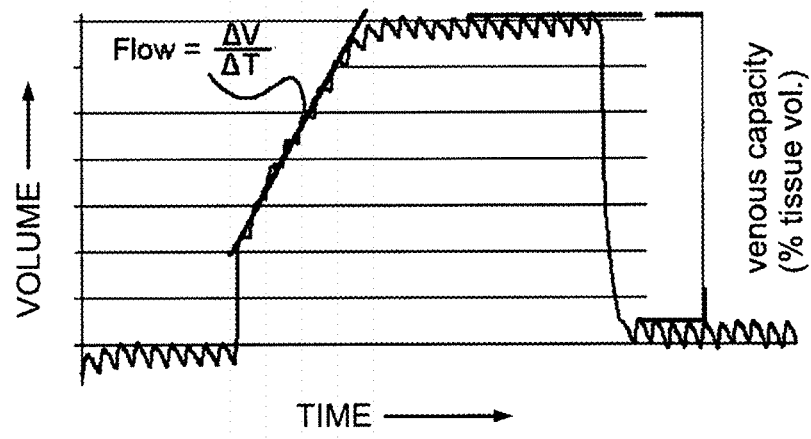
FIG. 1d illustrates the additional process for determining venous capacitance or compliance.

As shown in FIG. 1d, after sufficient time has passed to ensure that the veins have reached a plateau of volume at the given level of venous occlusion pressure, the total volume of accumulated blood may be determined. When this value is expressed as a percentage of the overall tissue mass of the tissues from which the measurement is derived, the venous capacitance may be calculated as the percent volume change for the given level of venous occlusion pressure.

As further described above, because of the hydrostatic pressure complement added to the venous pressure according to the vertical level of the measuring site with respect to the heart, the conventional VOP measurements have been limited to measurement of sites above the heart level.

As will be described more particularly below, according to the present invention the venous occlusion plethysmographic device is used, among other functions, to apply a pressure to the measurement site which counterbalances the combined inherent venous pressure plus the hydrostatic venous pressure at a given measurement site. This avoids venous distension due to the measurement site being below heart level, and depending on the level of pressure applied, thereby enables the VOP measurement method to be used at body regions at any level with respect to the heart level.

PREFERRED EMBODIMENTS OF THE INVENTION

Figure 2:
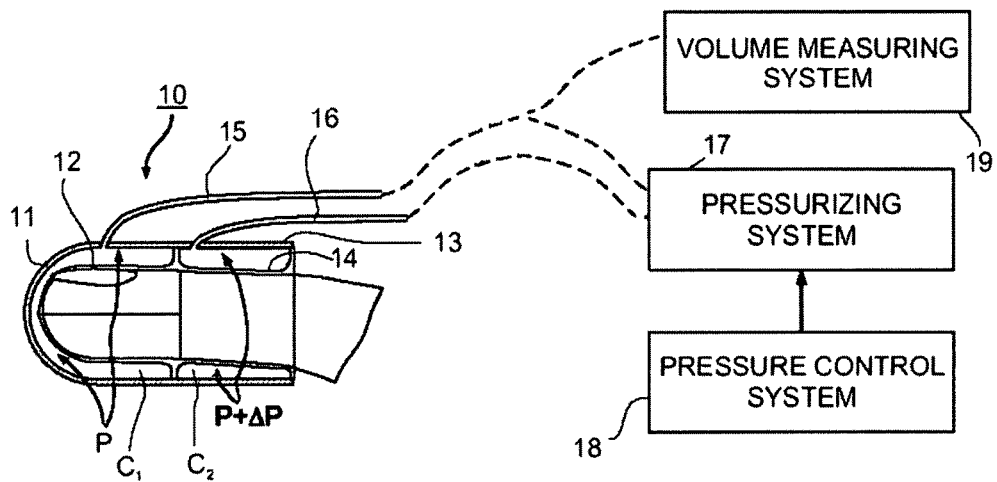
FIG. 2 illustrates one form of apparatus useful in accordance with the present invention for overcoming basic drawbacks of the conventional VOP measurement method and for enabling that method to be used for making measurements on body parts at any level with respect to the subject's heart.

FIG. 2 illustrates one form of apparatus which may be used for non-invasively measuring a physiological parameter of a subject in accordance with the present invention. The apparatus illustrated in FIG. 2 includes a peripheral arterial tonometry (PAT) probe constructed as described in the above-cited patents to be applied to a selected body region, a pressurizing system controlled to pressurize different sections of the probe in accordance with the present invention, and a measuring system for measuring volume changes in the body region as a result of the controlled pressurization changes applied to the body region. In the example illustrated in FIG. 2, the body region is a finger (or toe) of the subject.

Thus, the apparatus illustrated in FIG. 2 includes a PAT probe, generally designated 10, serving as the venous occlusion plethysmographic device. Probe 10 includes a housing having a first section 11 configured to enclose the distal tip of the finger and carrying, on its inner surface, a membrane 12 defining with housing section 11 a first fluid chamber $C_1$. Probe 10 includes a second housing section 13 of annular configuration so as to enclose the annular region of the subject's finger just inwardly of the distal tip. Housing section 13 also carries on its inner surface a membrane 14 defining a second fluid chamber $C_2$ adapted to enclose the annular region of the subject's finger inwardly of the distal tip.

The two chambers $C_1$, $C_2$ are connected via tubes 15 and 16, respectively, to a fluid pressurizing system 17, which is controlled by a pressure control system 18.

Volume measuring system 19 measures volume changes within chamber $C_1$, and thereby volume changes within the distal tip of the finger enclosed by the chamber, during the pressurizing of the two chambers $C_1$, $C_2$, as described below. Volume measuring system 19 also processes those volume changes in the manner described below, to thereby produce a measurement of the desired physiological parameter, e.g.

volumetric blood flow, as described above with respect to FIGS. 1a-1c, or the overall volume change at a given venous pressure as described in FIG. 1d. The above-cited US Patents on the PAT probe describe various systems that may be used for the volume measuring system 19.

The apparatus illustrated in FIG. 2 is used in the following manner in order to non-invasively measure a physiological parameter, e.g. volumetric blood flow, or venous capacitance, in the following manner:

First, chambers $C_1$ and $C_2$ are pressurized to a pressure P at least sufficient to compensate for the inherent venous pressure added to the maximal hydrostatic pressure due to the maximal possible vertical displacement of the body part with respect to the subject's heart level. For example, if the body part is the subject's finger, chambers $C_1$ and $C_2$ would be pressurized by pressurizing system 17 to apply, over the entire surface of the finger contained within the probe, a uniform pressure field (P) sufficient to compensate for the maximal hydrostatic pressure added to the venous pressure at any vertical level of the finger tip.

Pressuring system 17 is then controlled by pressure control system 18 to intermittently raise and lower the pressure (P) within chamber $C_2$ by a pressure increment ($\Delta$P) sufficient to produce the venous occlusion but below the arterial blood pressure, and then to reduce the pressure back to the constant pressure level (P) in $C_1$ as described above. As this is done, the changes in volume within chamber $C_1$, and thereby within the distal region of the subject's finger enclosed by chamber $C_1$, are measured by volume measuring system 19. Volume measuring system 19 also processes the measured volume changes within fluid chamber $C_1$ to provide a measurement of the particular physiological parameter desired to be measured.

FIGS. 1a-1c illustrate how the volume changes are measured and processed in order to produce a measurement of the quantitative blood flow. Thus, FIG. 1a illustrates the pressure increment to ($P_0+\Delta P$) intermittently applied to chamber $C_2$ so as to intermittently occlude the flow of venous blood in the annular region of the finger engaged by fluid chamber $C_2$; FIG. 1b illustrates the cumulative volume changes as sensed by sensor 19 within fluid chamber $C_1$ enclosing the distal tip of the subject's finger; and FIGS. 1c and 1d illustrate the manner in which the rate of the volume changes is used to provide a measurement of quantitative blood flow.

The PAT probe illustrated in FIG. 2 provides a number of very important advantages when used as the venous occlusion device in the above-described VOP measurement process. Thus, its annular fluid chamber $C_2$ may be used for applying the venous occlusion pressure to the finger, whereas its end chamber $C_1$ enclosing the distal tip region of the finger may be used for measuring volume changes in the distal tip region as a result of the venous occlusion produced by chamber $C_2$. In addition, the end chamber $C_1$ as well annular fluid chamber $C_2$ may be used for applying the counterbalancing pressure to the distal tip of the finger and the adjacent finger region in order to compensate for the hydrostatic pressure added to the venous pressure at the lowest vertical level of the finger with respect to the subject's heart level, thereby enabling the apparatus to be used with respect to a body part at any vertical level relative to the heart.

The above-described PAT probe is ideally suited for performing VOP type measurements at any level of elevation relative to heart level since it is specifically designed to be able to apply a uniform pressure field over the entire surface of the body part under study, including its distalmost end (e.g. the distal tip of the finger in the above-described example) while remaining firmly attached to it. Thus, as shown in FIG. 2, the PAT probe 10 can be used to produce in chambers $C_1$ and $C_2$ a pressure P sufficient to overcome the passive venous filling due to the inherent venous pressure, plus the hydrostatic effects within the entire measurement region, namely the region enclosed by chambers $C_1$ and $C_2$. The PAT probe 10 can also be used to induce venous occlusion by providing an increment in pressure ($\Delta$P) in the annular region of the finger enclosed by chamber $C_2$.

The consequences of the presence and absence of hydrostatic pressure induced venous distensions on the compliance of the veins is illustrated in FIGS. 3a, 3b and 4a, 4b.

Figure 3A:
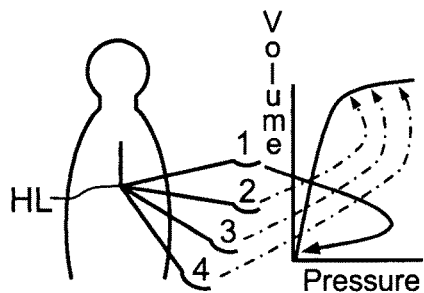
FIG. 3a illustrates an inherent drawback of the conventional VOP measurement systems presently in use in that in the absence of an appropriate level of externally applied counter pressure, the venous filling of the monitored site, e.g. a finger or toe, is progressively increased as the monitored site (arm or leg) is vertically lowered with respect to heart level. In contrast.
Figure 3B:
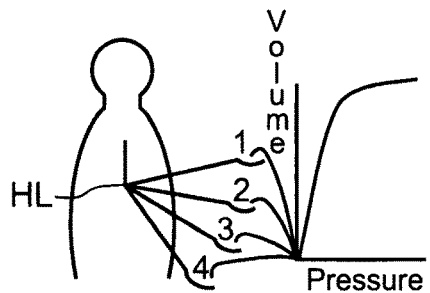
FIG. 3b shows that the provision of a sufficient level of externally applied pressure to counterbalance the intra-venous pressure, applied around the relevant body region up to and including its terminal extremity, will prevent the occurrence of venous filling due to vertical lowering with respect to heart level. To ensure the prevention of venous filling at all levels of vertical displacement below heart, the level of pressure must equal or exceed the sum of the inherent venous pressure plus the hydrostatic pressure at the maximal degree of vertical displacement.

FIGS. 3a, 3b illustrate the points of intra-venous pressure and volume along the venous compliance curve at various levels of displacement of the measurement site with respect to the heart level. Here it can be seen that in the absence of external counter pressure applied by the probe (FIG. 3a), the level of venous filling is progressively higher as the arm is lowered with respect to heart level. If however a sufficient level of probe pressure is applied to counterbalance the hydrostatic venous pressure, then venous distention due to lowering the measurement site below heart level can be avoided, as shown in FIG. 3b.

Similarly, when an incremental pressure is applied to the proximal venous occlusion cuff (as shown in FIG. 2), the increase in volume distal to the cuff will be dependent on the initial starting point of the venous pressure and corresponding volume along the venous compliance curve.

Figure 4A:
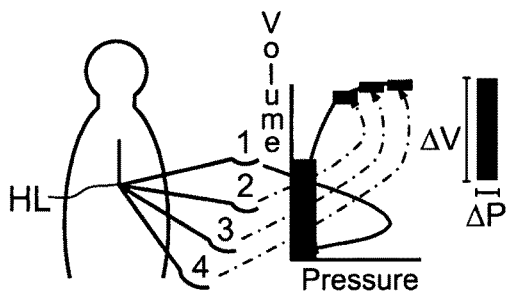
FIGS. 4a and 4b are diagrams, corresponding to those of FIGS. 3a and 3b, respectively, but illustrating how the use of the apparatus of FIG. 2 in 4b overcomes the above-described drawbacks in the conventional VOP measurement method to enable measurements to be made with respect to body parts at any desired vertical level with respect to the heart.
Figure 4B:
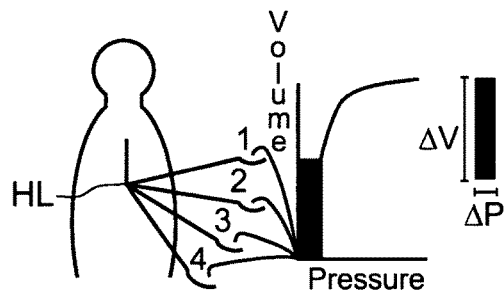

FIG. 4a shows that when venous occlusion pressure is applied to a system that does not have enough pressure to counterbalance the intra-venous pressure level, the added volume will be dependent on the beginning position on the venous compliance curve, since less venous volume change occurs for a given venous pressure change as compliance is reduced. If however a sufficient level of probe pressure is applied to counterbalance the overall intra-venous pressure, then added venous distention due to the venous occlusion pressure will cease to be dependent on the level of displacement of the measurement site with respect to heart level. This would therefore facilitate the accurate determination of blood flow irrespective of the measurement site location as demonstrated in FIG. 4b.

Figure 5:
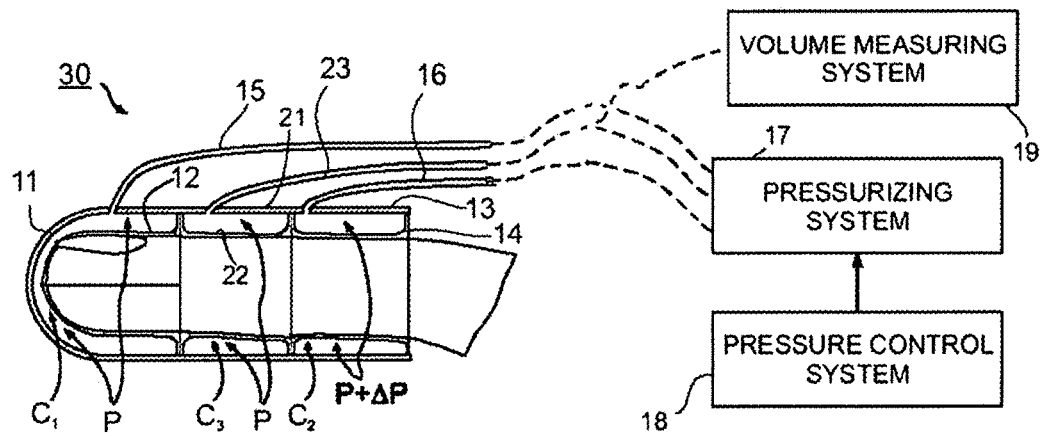
FIG. 5 illustrates another apparatus that may be used for measuring a physiological parameter in accordance with the present invention.

FIG. 5 illustrates apparatus similar to that of FIG. 2, but using a PAT probe, therein generally designated 30, of the three-section type, as described in the above-cited U.S. Pat. No. 6,488,633, as the venous occlusion device. To facilitate understanding, those elements in the probe of FIG. 5 common to the probe of FIG. 2 are identified with the same reference numerals.

Thus, probe 30 illustrated in FIG. 5 also includes a first housing section 11 carrying a first membrane 12 defining a first fluid chamber $C_1$, and a second housing section 13 carrying a second membrane 14 defining a second fluid chamber $C_2$. In this case, however, the two housing sections 11 and 13 are not contiguous, as in FIG. 2, but rather are spaced from each other by a third housing section 21 carrying a third membrane 22 defining a third fluid chamber $C_3$; chamber $C_3$ communicates with the pressurizing system 17 via a third tube 23.

In this case, the two distal chambers $C_1$ and $C_3$ are maintained at a common pressure (P), sufficient to compensate for the maximal hydrostatic pressure due to vertical displacement, added to the inherent venous pressure. The proximal chamber $C_2$ defined by housing section 12 serves, as in the probe of FIG. 2, as the occluding section which is intermittently raised above the pressure level (P) sufficient to compensate for the maximal hydrostatic pressure plus the inherent venous pressure applied to $C_1$ and $C_3$, by the incremental venous occlusion pressure (P+ΔP) but below the arterial pressure, as described above with respect to FIG. 2. The volume measuring system 19 measures the changes in volume in the region of the distal tip of the subject's finger enclosed by chamber $C_1$. The changes in volume are utilized to provide a measure of the particular physiological parameter, e.g. volumetric blood flow (BF) as described above with respect to FIG. 2.

It will thus be seen than the three-section probe illustrated in FIG. 5 operates in substantially the same manner as described above with respect to FIG. 2, except that the intermediate fluid chamber $C_3$, defined by the intermediate housing section 21, serves as an isobaric (equal-pressure) intermediate region to avoid the mechanical perturbation of the changes in fluid chamber $C_2$ being directly transmitted to fluid chamber $C_1$.

An additional way in which the three compartment design can be used is to provide pressurizing means which would allow all three compartment to be independently pressurized, and to use the first two compartments (i.e. those corresponding to $C_3$ and $C_2$) in FIG. 5 for measuring the accumulation of venous blood in the manner described above, (the one nearest the heart producing the venous occlusion pressure, while the middle one is used to accumulate the venous blood), while the third compartment (the one furthest from the heart), serves to arrest the circulation in the body region which is distal or down stream from the heart in the direction of the blood flow). In this manner, the measurement site need not necessarily extend to and include the terminal most extremity of the body region being measured, but may in fact be a predetermined region preceding it.

In addition to the fingers or toes, other body regions may also be measured in accordance with any of the above described methods, using PAT probes of two or more compartments, particularly as described in our pending International Application (WO 02/080752) PCT/IL02/00249. The latter application describes the applicability of the multi-compartment probe in the measurement of more extensive body regions such as the upper and lower limbs.

Figure 6:
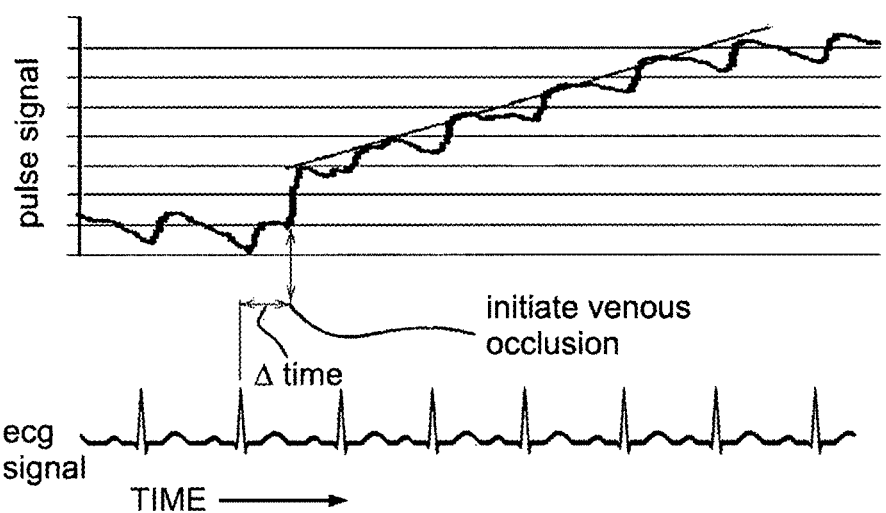
FIG. 6 illustrates a variation wherein the subject's ECG signal is used for triggering the start of the venous occlusion.

ECG signal may be used for triggering the start of the venous occlusion to a defined point in time relative to the heart cycle. FIG. 6 shows how the initiation of a VOP measurement is triggered by the ECG signal to determine the start of the measurement with respect to the heart cycle. This is important in standardizing the measurement since with very large pulse volumes, filling of the veins may occur within a small number of pulses, and the point of commencement may be critical. A direct-contact displacement-type sensor or acceleration-type sensor may be used for this purpose, in which case the monitored parameter for triggering the start of venous occlusion would be some predetermined landmark of the pulse signal detected either at the measurement site or at another part of the body. Likewise, the actual signal detected by the PAT probe can be used as the monitored parameter for triggering the start of venous occlusion based on the detection of a predetermined landmark of the pulse signal detected by the PAT probe at the measurement site.

There are several direct applications for which improved BF measurements in accordance with the present invention would be very useful;

A) In general research/clinical research spheres, BF determination without restriction of the vertical displacement of a finger or another body part being measured, would facilitate the study of the effect of drugs, in particular those with vasoactive effects, or any other interventions, as well as being particularly useful for measuring blood flow during natural orthostasis, tilt testing procedures, etc., in which the body undergoes changes in its orientation with respect to gravity.

B) During testing of endothelial function as described in our earlier U.S. Pat. No. 6,939,304, measuring BF immediately following blood flow occlusion could provide an objective index of the size of the acute peak hyperemic level. This would for example help normalize the subsequent post ischemic PAT response. Determining pre-occlusion BF, and the relative change following occlusion could also be useful to this end. Such evaluations would also be useful in relation to other stimuli for eliciting endothelial activity which are known to the art such as the intra-arterial injection of acetylcholine.

C) By monitoring both PAT signal amplitude and BF as determined in the above described manner, the predominant site of vascular responses (terminal versus more central) could be determined. This would be based on the concurrently measured relative changes of these two parameters since BF increase represents a reduction in the resistance of the smaller resistance vessels, whereas an increase in PAT signal amplitude at fixed level of BF represents a reduction in the resistance of the larger more central conducting vessels. If for example the relative increase in the PAT signal is greater than that of the BF, then it may concluded that the vascular effect was predominant in larger more central vessels, and vice-versa, D) This method could be used to provide on-line feed back of the level of venous distention, thereby enabling the measurement system to be potentially able to avoid reaching a state of venous over-distention.

E) Combining PAT signal measurements and periodic BF measurements during the pre and post occlusion periods could be used to more comprehensively define the degree and nature of the induced vascular response.

F) Measurement of the tissue volume of the tissue mass from which the VOP is being measured may also be used to provide a blood flow rate measurement relative to the tissue mass, thus providing measurement values expressed as volume per unit tissue volume per unit time. Tissue mass and absolute volume can be measured in accordance with known techniques or those described in our pending International Application WO 2004/041079. The volumetric calibration of blood flow and of tissue volume will facilitate the accurate determination of blood flow in units of volume per time per unit tissue volume. Likewise the venous capacitance can be expressed in units of percentage change of the tissue volume.

Figure 7:
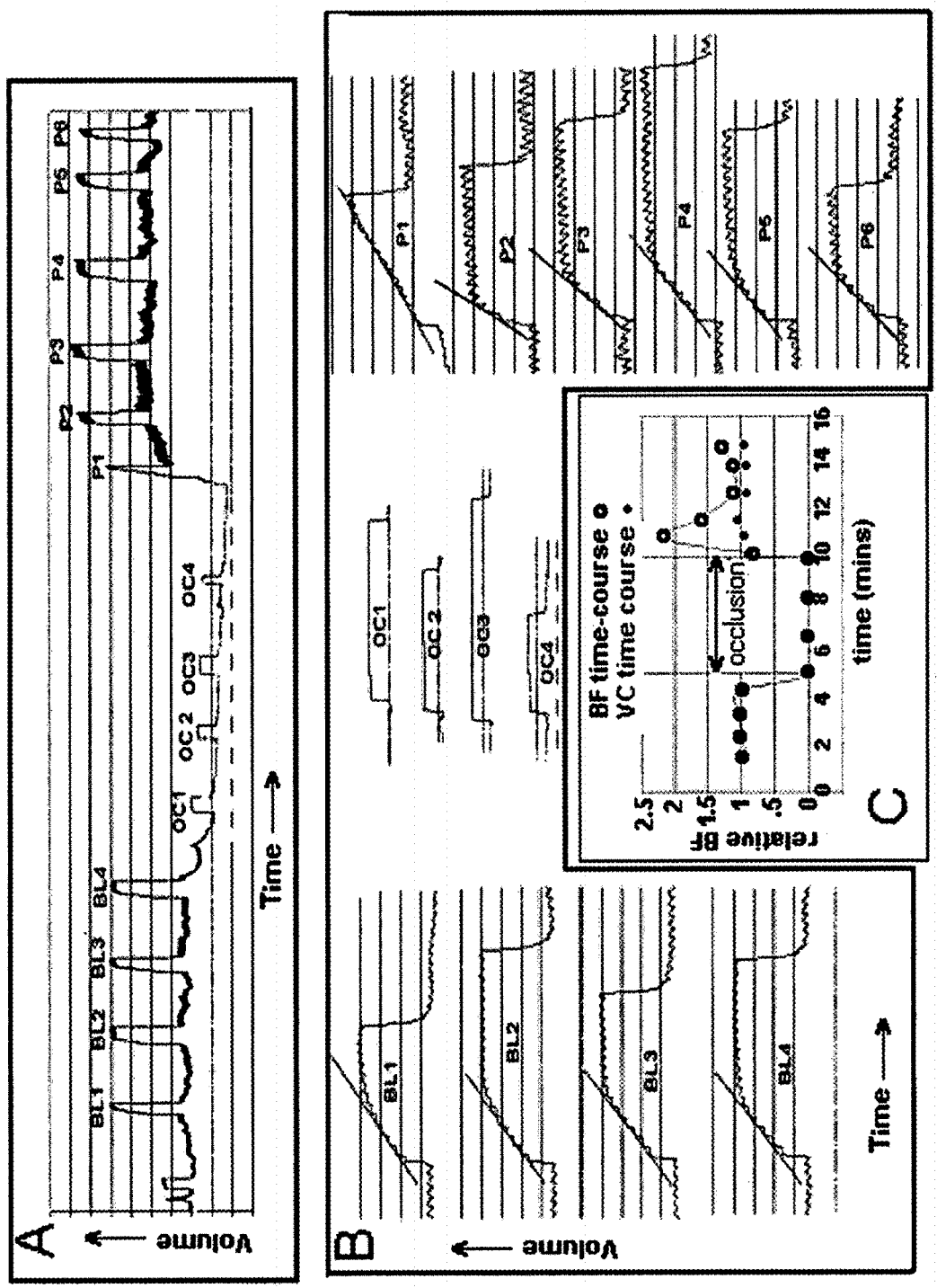
FIG. 7 includes a plurality of panels illustrating how the blood flow measurements may also be used in connection with endothelial function measurements.

The blood flow measurements may also be used in relation to the testing of reactive hyperemia in general, and reactive hyperemia in specific relation to endothelial function measurements. FIG. 7, Panel A shows the time course of a series of venous occlusion plethysmographic measurements related to a measurement of endothelial function in accordance with our U.S. Pat. No. 6,939,304. Panel B shows in greater detail the individual venous occlusion measurements corresponding to the baseline (BL), occluded (OC) and post occlusion (P), measurements designated in panel A. Panel C shows the time course of blood flow rates relative to the mean baseline value throughout the study (larger open circle), as well as the time course of venous capacity relative to the mean baseline value throughout the study (smaller closed circles).

Similarly, provided that sufficient time is allowed for the veins to reach a state of complete filling, venous capacity measurements may also be derived in relation to the testing of reactive hyperemia, as can be appreciated from Panels A and B in FIG. 7.

Of special note, it may be further appreciated that an artifact associated with the mechanical perturbation due to the initiation of the venous occlusion process is apparent in all of the individual measurements. This transient change is a known phenomenon associated with VOP measurements. For calculating blood flow, this part of the signal is simply avoided and the calculation of blood flow is based on the signal following it.

With regard to the cumulative volume calculation, the artifact may be avoided by measuring the volume change occurring during the transition between a state of complete venous filling and subsequent venous emptying after the venous occlusion has been removed. This was illustrated in FIG. 1d, and the relative venous capacity values in this case are shown in Panel C of FIG. 7. The magnitude of the volume artifact may be quantified by measuring it during a state of arrested blood flow such as during a period of blood flow occlusion, as shown in measurements OC1-OC4.

It is to be noted that the measurements of peripheral arterial tone and of the blood flow were all derived from the same probe, wherein the pressure of the compartment nearest the heart was intermittently varied as shown in FIG. 1a. The measurements may also be made by concurrently comparing one body region being tested to another serving as a control. Examples include corresponding fingers of opposite sided hands when a test is preformed on one of the arms; or paired fingers of a hand when a test is preformed on one of the fingers. An example of such a measurement is shown in FIG. 8 which illustrates the parallel time courses of the occluded and control sides in which the individual venous occlusion measurements corresponding to the baseline (BL), occluded (OC) and post occlusion (P), measurements may be seen.

Figure 8:
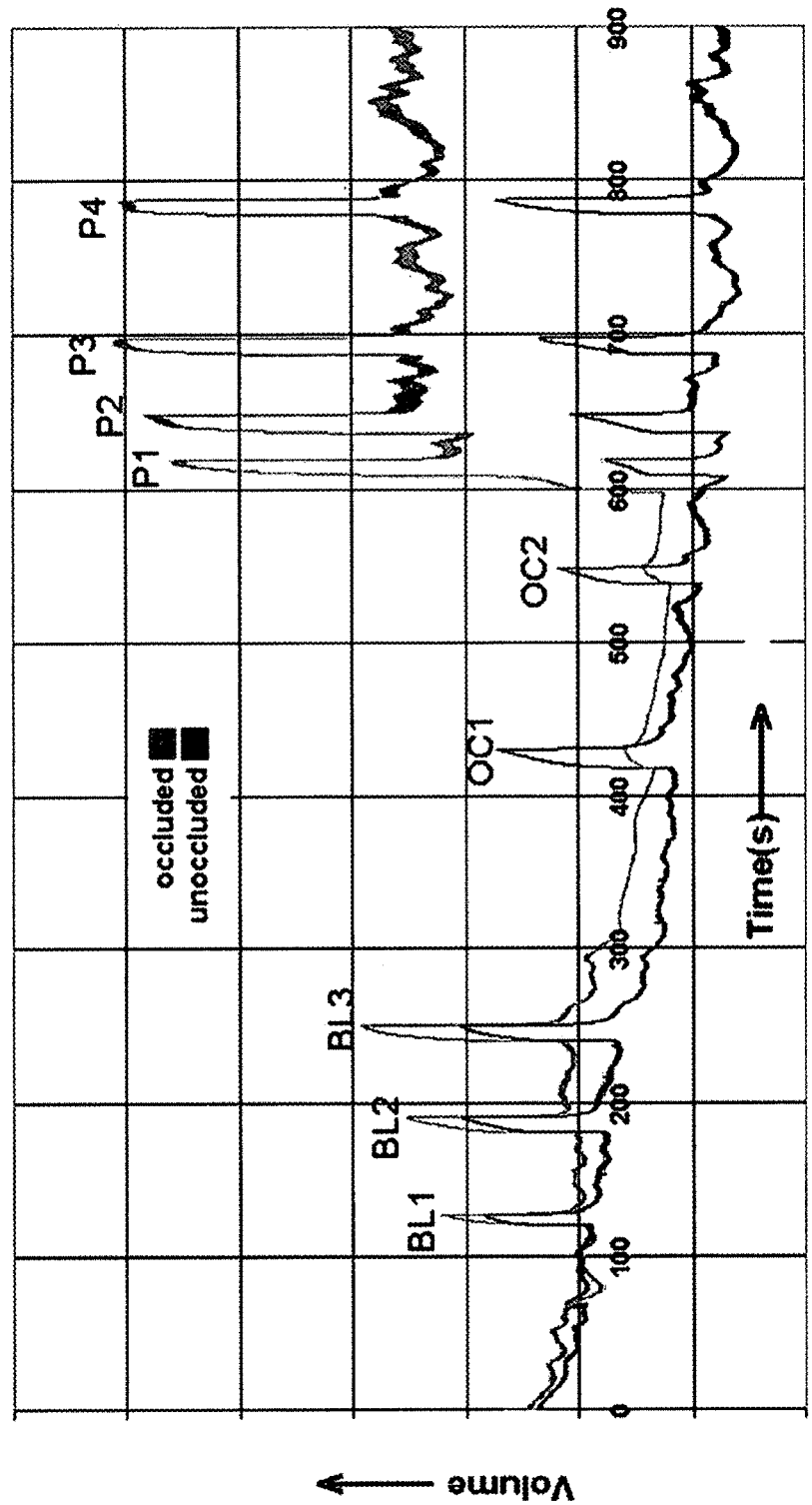
FIG. 8 illustrates concurrently comparing the measurements of one body region being examined with measurements of another body region serving as a control.
Figure 9A:
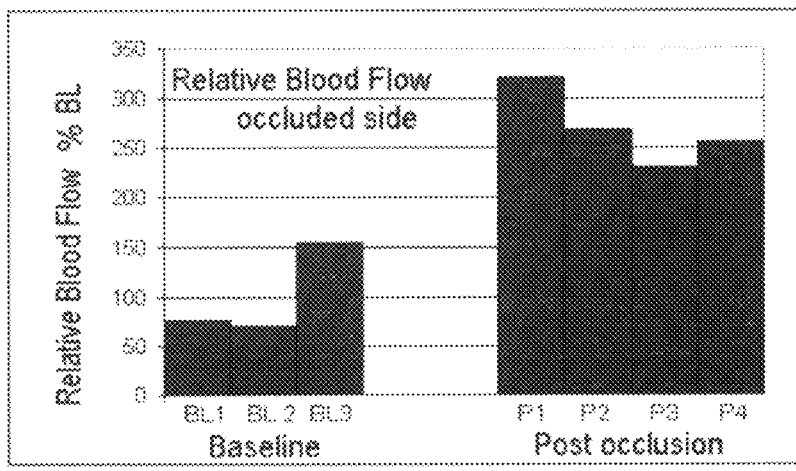
FIGS. 9a-c illustrate one manner of generating an index of blood flow corrected for extraneous influences which affect both control and tests sites.
Figure 9B:
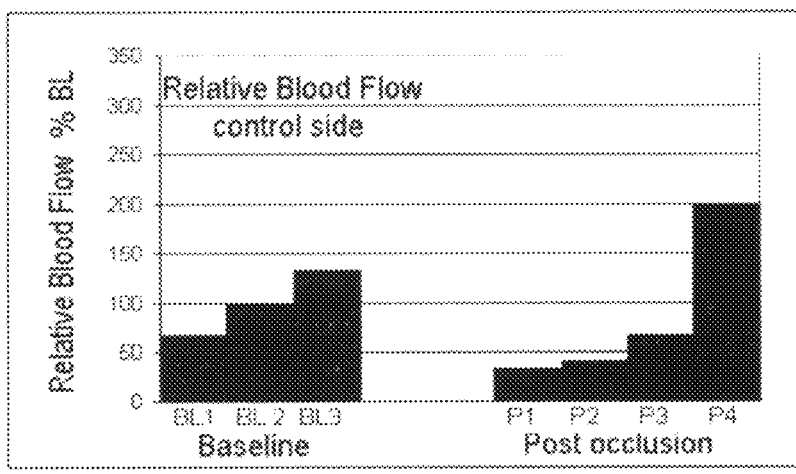
Figure 9C:
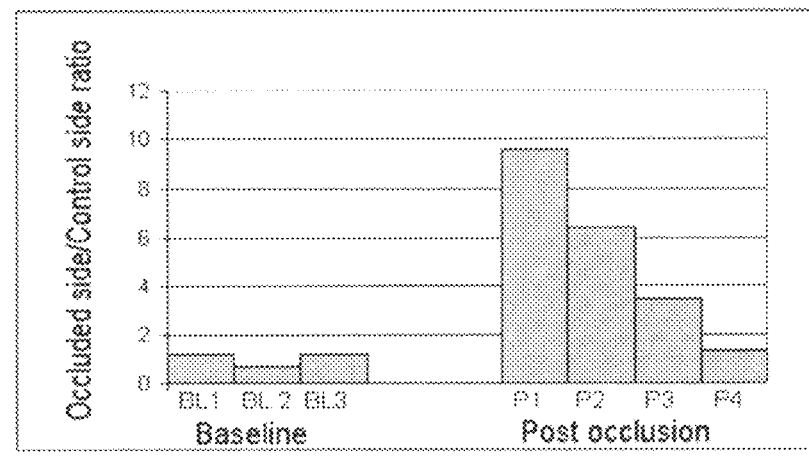

FIG. 9 illustrates in histogram form the results of respective serial blood flow determinations of the arm with blood flow occlusion (Panel A), and of the arm without blood flow occlusion (Panel B) corresponding to the measurements shown in FIG. 8. In both cases, the pre-occlusion and post-occlusion values are shown with the corresponding labeling of baseline (BL), occluded (OC) and post occlusion (P) times of the individual measurements corresponding to FIG. 8. The values may be expressed in absolute terms, or as in the illustrated example, may be expressed as percentages of the average pre-occlusion values.

Panel C of FIG. 9 shows one manner in which the corresponding occluded and control side blood flow rate values can be used to generate an index of corrected blood flow, which is intended to provide the flow rate change due to the test stimulus per se, that is, after being corrected for extraneous influences which affect both control and test sites. In this case, the test response, relative to its average baseline flow rate, is expressed as a ratio of the corresponding control side value.

Alternative ways of correcting for the extraneous influences which affect both control and test sites (not shown here), include subtracting the corresponding control value from that of the stimulated site. This may further be done by using absolute blood flow rate values, or by using blood flow rate values which are relative to their respective initial baselines.

While the general principles described herein have been illustrated with examples based on finger probe measurements, it will be understood that many other types of plethysmographic devices, such as those described in our above-cited International application published as International Publication No. WO 02/080752, can be used, and measurements can be made from a wide range of body sites as further described in that application.

The invention can be implemented in methods and apparatus for measuring a wide variety of physiological parameters with respect to a finger another body part without restriction of the vertical displacement relative to heart level, including: blood flow rate relative to tissue volume; venous capacity at a given pressure level; and venous capacity expressed as a percentage of the tissue volume per unit pressure. The invention may also be used: to facilitate the study of the effect of drugs, in particular those with vasoactive effects; to facilitate the study of blood flow during natural orthostasis, tilt testing procedures, or where the body undergoes changes in its orientation with respect to gravity; and in conjunction with a study of an eliciting stimulus to measure endothelial function. For example, a comparison may be made of blood flow before and after application of an eliciting stimulus such as a period of blood flow occlusion, to provide an objective index of the magnitude of the vascular response to the endothelial eliciting stimulus.

The invention may also be implemented in apparatus where measurements of peripheral arterial tone and blood flow are derived from the same probe, or wherein measurements of peripheral arterial tone and venous capacity are derived from the same probe.

Other possible applications of the invention include those wherein one probe is applied to a body location to receive a vasoactive stimulus, one probe is applied to a homologous or paired body part not to receive a vasoactive stimulus, and respective changes in the blood flow or venous capacity are used to compensate for spontaneous short-term shifts in the blood flow or venous capacity of local or systemic origin. The homologous or paired body parts receiving or not receiving the vasoactive stimulus for measuring respective changes in the blood flow or venous capacity therein could be corresponding fingers of opposite sided hands, or paired fingers, or toes of a hand or a foot when a test is performed on one of the fingers but not on the other. The changes in the blood flow or venous capacity in the body location to receive a vasoactive stimulus may be expressed as a function of the changes in the blood flow or venous capacity in the body location not to receive a vasoactive stimulus, to compensate for spontaneous short-term shifts in the blood flow or venous capacity of local or systemic origin.

The invention could also use comparative changes of peripheral arterial tone and blood flow to determine the predominant site of vascular responses, or to provide on-line feed-back of the level of venous distention to avoid reaching a state of venous over-distention. The comparison of blood flow before and after application of the eliciting stimulus may be expressed as an absolute difference, or as a relative change of the post-occlusion value to the baseline flow.

It will be appreciated, therefore, that the preferred embodiments of the invention described herein are set forth merely for purposes of example, and that many other variations, modifications and applications of the invention may be made.

What is claimed is:

1. A method for non-invasively measuring a physiological parameter of a subject, comprising:

applying to a body part of the subject a venous occlusion plethysmographic device including a first section and a second section, the applying comprising engaging the first section with a first engaged extent of a distal region of the body part including its distal tip, and engaging the second section with a second engaged extent of a proximal region of the body part;

wherein the second engaged extent is adjacent to said first engaged extent at the side thereof facing the direction of venous blood flow toward the heart of the subject;

pressurizing said first section to produce a static pressure field therein in which the pressure applied to at least a part of said first section exceeds the sum of the inherent venous pressure and the hydrostatic pressure prevailing within said body part;

intermittently raising and lowering the pressure in said second section to a pressure above or equal to the pressure within said first section but below the arterial blood pressure;

measuring changes in volume of said first engaged extent of the body part;

and utilizing said measured changes in volume to provide a measure of said physiological parameter.

2. The method according to claim 1, wherein said measured changes in volume are determined by measuring the volume changes at some given pulsewave landmark over at least a single pulse cycle.

3. The method according to claim 1, wherein said measured changes in volume are accumulated over a measured time period, and the rate of change is determined to thereby provide a measurement of volumetric blood flow.

4. The method according to claim 1, wherein said measured changes in volume are accumulated for sufficient time to reach a plateau, and the volume of accumulated blood is determined to thereby provide a measurement of venous capacitance at the higher level of pressure in said second section.

5. The method according to claim 1, wherein said first section includes a first chamber for applying said static pressure to said distal region including its distal tip, and said second section includes a second chamber for applying said intermittently raised and lowered pressure to said proximal region.

6. The method according to claim 5, wherein said first chamber is configured to engage said distal region including its distal tip of the body part.

7. The method according to claim 5, wherein said first section further includes a third chamber on the proximal side of said first chamber such that said first chamber pressurizes a portion of said distal region of the body part including its distal tip, and said third chamber pressurizes said distal region of the body part between said portion and said second engaged extent.

8. The method according to claim 7, wherein the pressures in said first and third chambers are the same and each exceeds the sum of the inherent venous pressure and the hydrostatic pressure prevailing within said body part.

9. The method according to claim 7, wherein the pressure in said first chamber is sufficient to arrest the circulation in said distal tip, and the pressure in said third chamber exceeds the sum of the inherent venous pressure and the hydrostatic pressure prevailing within said body part.

10. The method according to claim 1, wherein said body part is a finger or toe of the subject.

11. The method according to claim 1, wherein the subject's ECG signal is sensed and used for triggering the intermittent raising and lowering of the pressure in said second section.

12. The method according to claim 1, wherein said measurement of volumetric blood flow is made in conjunction with a study of an eliciting stimulus to measure endothelial function of the subject.

13. The method according to claim 1 wherein said physiological parameter is peripheral arterial tone and volumetric blood flow, and wherein peripheral arterial tone and volumetric blood flow measurements are derived from the same said venous occlusion plethysmographic device.

14. The method according to claim 1, wherein said changes in volume of said first region of the body part are expressed relative to the volume of said first region of the body part.

15. Apparatus for non-invasively measuring a physiological parameter of a subject, comprising:

a venous occlusion plethysmographic device including a first section configured to engage a first engaged extent of a distal region of the body part including the distal tip, and a second section configured to engage a second engaged extent of a proximal region of the body part;

wherein the second engaged extent is adjusted to said first engaged extent at the side thereof facing the direction of venous blood flow toward the heart of the subject;

a pressurizing system for pressurizing said first section to produce a pressure field therein in which the pressure applied to at least a part of said first section exceeds the sum of the inherent venous pressure and the hydrostatic pressure prevailing within said body part;

and a control system for intermittently raising and lowering the pressure in said second section to a pressure above or equal to the pressure in said first section but below the arterial blood pressure, for measuring changes in volume of said first region of the body part, and for utilizing said measured volume changes to provide a measure of said physiological parameter.

16. The apparatus according to claim 15, wherein said control system accumulates said measured changes in volume over a measured time period, and determines the rate of change to thereby provide a measurement of volumetric blood flow.

17. The apparatus according to claim 15, wherein said control system accumulates said measured changes in volume for sufficient time to reach a plateau, and determines the volume of accumulated blood to thereby provide a measurement of venous capacitance at the higher level of pressure in the said second section.

18. The apparatus according to claim 15, wherein said first section includes a first chamber for applying said static pressure to said distal region, including its distal tip, and said second section includes a second chamber for applying said intermittently raised and lowered pressure to said proximal region.

19. The apparatus according to claim 18, wherein said first chamber is configured to engage said distal region including its distal tip of the body part.

20. The apparatus according to claim 19, wherein said first section further includes a third chamber on the proximal side of said first chamber such that said first chamber pressurizes a portion of said distal region of the body part including its distal tip, and said third chamber pressurizes said distal region of the body part between said distal portion and said second engaged extent.

21. The apparatus according to claim 20, wherein said control system controls the pressure in said first and third chambers to be the same and to exceed the sum of the inherent venous pressure and the hydrostatic pressure prevailing within said body part.

22. The apparatus according to claim 20, wherein said control system controls the pressure in said first chamber to be sufficient to arrest the circulation in said distal region including its distal tip, and the pressure in said second chamber to exceed the sum of the inherent venous pressure and the hydrostatic pressure prevailing within said body part.

23. The apparatus according to claim 15, wherein said body part is a finger or toe of the subject.

24. The apparatus according to claim 15, wherein said control system includes a sensor for sensing the subject's ECG and for using same to trigger the intermittent raising and lowering of pressure in said second section.

25. The apparatus according to claim 15 wherein said physiological parameter is peripheral arterial tone and volumetric blood flow and wherein peripheral arterial tone and volumetric blood flow measurements are derived from the same said venous occlusion plethysmographic device.

26. The method according to claim 15 wherein said changes in volume of said first region of the body part are expressed relative to the volume of said first region of the body part.

27. The method of claim 1, wherein said engaging comprises a contiguous engagement of the first and second engaged extents.

28. The apparatus of claim 15, wherein the first and second sections are arranged to define a contiguous engagement of the body part including the first and second engaged extents when the first and second sections engage the body part.

29. The method of claim 1, wherein the pressurizing and intermittent raising and lowering of pressure is such that hydrostatic pressure due to said body part being at a low vertical level with respect to heart level is counterbalanced in said body part distal to said second region, when said first region is so-hydrostatically pressurized, and such that induction of venous distension distal to said second region is avoided.

30. The method of claim 7, wherein said first, second and third chambers are arranged to define a contiguous engagement of the body part.

31. The apparatus of claim 20, wherein said first, second and third chambers are arranged to define a contiguous engagement of the body part.

* * * * *